United States Patent [19]

Dickoré et al.

[11] 4,035,364
[45] July 12, 1977

[54] METHYL BROMIDE THIOL METHYLATION OF MERCAPTO GROUP OF 4-AMINO-6-T.-BUTYL-3-MERCAPTO-1,2,4-TRIAZIN-5-ONE

[75] Inventors: Karlfried Dickoré; Walter Merz, both of Leverkusen; Johann Dahm, Dormagen, all of Germany; Donovan Norman Smith, Jr., Kansas City, Mo.

[73] Assignees: Bayer Aktiengesellschaft, Leverkusen, Germany; Mobay Chemical Corporation, Pittsburgh, Pa.

[21] Appl. No.: 708,674

[22] Filed: July 26, 1976

[51] Int. Cl.² ........................................ C07D 253/06
[52] U.S. Cl. ............................................ 260/248 AS
[58] Field of Search ............................. 260/248 AS

[56] References Cited

U.S. PATENT DOCUMENTS 3,897,429   7/1975   Haglid ..................... 260/248 AS

*Primary Examiner*—John M. Ford
*Attorney, Agent, or Firm*—Burgess, Dinklage & Sprung

[57] ABSTRACT

In the methylation of 4-amino-6-t.-butyl-3-mercapto-1,2,4-triazin-5-one to produce 4-amino-6-t.-butyl-3-methylmercapto-1,2,4-triazine-5-one using methyl bromide, the reaction is run in the absence of air whereby product coloration is avoided. Desirably considerable agitation is employed along with recycle and especially with an emulsifying agent which markedly speeds up the reaction. Measures such as operating under a slight vacuum and recycle of unused methyl bromide and mother liquor are employed to improve the yield and to avoid the problems of discharging the bromides to the environment.

7 Claims, No Drawings

METHYL BROMIDE THIOL METHYLATION OF MERCAPTO GROUP OF 4-AMINO-6-T.-BUTYL-3-MERCAPTO-1,2,4-TRIAZIN-5-ONE

The present invention relates to improvements in the methylation of 4-amino-6-t.-butyl-3-mercapto-1,2,4-triazin-5-one, hereinafter referred to as "butylthion", to produce 4-amino-6t.-butyl-3-methylmercapto-1,2,4-triazine-5-one, sometimes hereinafter referred to as "metribuzin."

U.S. Pat. No. 3,897,429 disclosed the methylation of butylthion in an alkaline medium with methyl bromide to produce metribuzin which is a herbicide of outstanding activity; actually methyl iodide is preferable but its cost is excessively high. In attempting to put the use of methyl bromide into commerical practice, however, it was found that the product occasionally was colored red where it should have been colorless. In addition, there were process losses which raised the cost to the point where processing with the bromide was not materially cheaper than use of the iodide. Further, it was found the reaction was relatively slow and presented certain safety hazards since methyl bromide is toxic.

It is accordingly an object of the present invention to provide a process utilizing methyl bromide as the methylating agent but not suffering from the above-mentioned disadvantages.

These and other objects and advantages are realized in accordance with the present invention pursuant to which the reaction is effected in the substanial absence of air, whereby there results a slurry from which substantially colorless solid product can be separated by settling, filtration, centrifugation or the like.

This is best effected by conducting the reaction in a closed vessel and removing all air prior to introduction of the methyl bromide. Thereafter the methyl bromide will vaporize, if added as a liquid, until it fills any gas space above the liquid in the vessel. There is advantageously employed a valve controlling the introduction of the methyl bromide so that the pressure in the gas space cannot rise above about 1.1 bars, i.e. when the pressure rises to that level the valve is closed and methyl bromide supply is interrupted. In the course of time the methyl bromide reacts and the pressure therefore drops, whereupon methyl bromide supply is resumed.

During the major portion of the reaction the pressure is below atmospheric, e.g. about 800 millibars. This prevents escape of any vapors of methyl bromide which is toxic.

Pressure is also employed as a means of monitoring the reaction since it falls as methyl bromide is consumed. Thus, when the pressure fails to fall after a certain time interval it is an indication that the reaction is complete. Accordingly, there is no need for stoichiometric analysis or extensive analysis of the starting material which may not be absolutely pure. This eliminates waste while at the same time simplifying the process. Higher pressures than atmospheric could similarly be employed with corresponding controls for the methyl bromide feed, but the excess or waste methyl bromide would be greater.

The reaction itself is conducted in an aqueous alkaline medium, i.e. at a pH of about 10 to 12. Any alkali can be employed bu alkali metal hydroxides and carbonates, especially sodium hydroxide, is preferred.

There must of course at least be sufficient alkali present to react with the butylthion and form the sodium salt, for example, and sufficient water to dissolve the butylthion salt. The temperature is not critical and may range from about 15° to 40° C and preferably about 30° to 35° C.

The reaction time depends upon the other parameters but can be reduced by one-half or more by use of an emulsifier, e.g. about 0.1 to 1% by weight and especially about 0.2 to 0.6% by weight of the entire solution. One particularly suitable class of emulsifiers is the alkyl aryl polyglycol ethers, e.g. nonyl phenol polyglycol ether (NP 10), but others also perform satisfactorily.

In such a system there is desirably considerable agitation to speed up the reaction and even a recirculation pump. Advantageously the methyl bromide point of introduction into the system is through a drip opening into the outlet line, i.e. pressure side, of the recirculation pump so as to effect rapid distribution and reaction. If no recirculation pump is used then a fine droplet dispersing head should be employed. Other means are to add the methyl bromide to the top of a fast running agitator.

After all the methyl bromide supply has been discontinued it is advantageous to hold the mass at reaction temperature for about an hour.

Advantageously the reaction is effected in a system comprising a reactor and dissolving vessel. Solution of the butylthion in aqueous alkali is effected in the dissolving vessel while the methylation is conducted in the reactor. At the end of the reaction in the reactor, nitrogen gas under pressure is supplied as a purge and nitrogen together with any vapors passes through a dip-tube into the dissolving vessel which contains butylthion in solution. This consumes the toxic methyl bromide vapors without losing them from the process. Alternatively, but less desirably, the vapors can be absorbed, as on charcoal, and later desorbed for recyclinng to another methylation cycle. Liquid absorption can also be employed as well as direct passage to the dissolving vessel without nitrogen but using vacuum or a pump to effect the transfer.

The contents of the reactor are filtered or centrifuged to remove the solid product metribuzin and leave a solution containing sodium bromide and some dissolved metribuzin product. Part of the filtrate is transferred to the dissolving vessel so as not to lose its values and also to build up its sodium bromide content to the maximum extent for later recovery. This recycling of the mother liquor is economically advantageous because in the manner the total amount of filtrate which has to be concentrated for methyl bromide recovery is substantially reduced.

All liquids can then be concentrated to dryness and the resulting solids, principally sodium bromide, reacted with sulfuric acid and methanol in known manner to regenerate methyl bromide for use in the described invention. Alternatively, they may be partially concentrated and similarly treated but this is less desirable because of a lower overall methyl bromide recovery.

The invention will be further described in the following illustrative examples wherein all parts are by weight unless otherwise expressed.

EXAMPLE 1.

To carry out the process there are employed two vessels, one serving as a dissolving vessel and the other as a reactor. While the reactor is in its final reaction stage, the dissolving vessel is charged with 1500 liters of water and 2500 kg of water-wet butylthion containing about 75% of solid material (approx. 9375 moles of butylthion). To this slurry there is added approximately 90% of the sodium hydroxide required to dissolve the butylthion, viz. 675 kg = 440 liters of 50% NaOH. The vessel is agitated. In the meantime the alkylation reaction is completed and the excess of methyl bromide is transferred from the reactor into the dissolving vessel, by a nitrogen purge. Specifically the reactor is pressurized with nitrogen up to 1.3 bars and then a valve between the vessels is opened to allow the nitrogen/methyl bromide gas mixture to be purged via a dip pipe into the dissolver. The reactor is purged for 30 minutes with a nitrogen stream until all methyl bromide is removed. Removal of all methyl bromide is essential because of the high toxicity of this material. The mixture is therefore tested for complete removal of methyl bromide before the product slurry is discharged to the filtration equipment. After the reactor has been emptied, the next charge from the dissolver is dropped into the reactor together with 1200 liters of wash water which had just been used for cleaning the dissolver.

Before any methyl bromide is added to the reactor the following operations are performed: agitation in the reactor is commenced, recirculation is started by means of a pump, and the pH of the solution is adjusted to 11.5–12.0 by addition of the remaining 10% of sodium hydroxide solution.

The reactor is then evacuated by means of a vacuum pump and the pressure inside the vessel is reduced to 100 millibars. After disconnecting the vacuum pump, the charging of the methyl bromide is started. The methyl bromide is injected into the return line of the recirculation pipe shortly behind the outlet of the pressure side of the pump. The temperaure in the reaction vessel is kept at 30°–35° C by brine cooling and the pH is maintained by the addition of caustic. Methyl bromide is charged into the reactor at a rate of 200 kg per hour. A valve interrupts methyl bromide addition if the pressure in the alkylation reactor exceeds 1.1 bars. As soon as the reaction is finished excess methyl bromide builds up a pressure inside the vessel that quickly reaches the set-point so the methyl bromide supply is shut off; in this way it is not neccessary to control the amount of methyl bromide by a weighing procedure because the addition is terminated by the excess of the alkylation reagent. Furthermore always having a small negative pressure inside the alkylation reactor (except upon completion of the alkylation) reduces the possiblity of methyl bromide leaks into the plant area. The absence of oxygen influences the color of the product favorably. After the addition of the methyl bromide- usually 880°–920° kg - post-reaction is carried on for 1 hour. To remove the excess methyl bromide present in the alkylation reactor, the vessel is pressurized with nitrogen up to 1.3 bars and a vent line to the solution vessel is opened. The excess methyl bromide is now stripped from the product slurry into the solution tank, which in the meantime has been charged with a new butylthion sodium salt solution.

The solution tank is equipped with a gas condenser, where escaping methyl bromide is condensed from the nitrogen stream, which is finally fed into a waste air incineration unit. The nitrogen purge is continued for 30 minutes; after this period the product slurry from the reactor is discharged to a pressure nutsch or a centrifuge and separated from the mother liquor. The reactor is now ready to receive the next batch from the solution vessel.

Starting from 9375 moles of butylthion, the usually obtainable yield for one reactor batch is 1906 kg of crude metribuzin (i.e. approx. 95% of the theory), said crude product containing about 4% of the isomeric N-methyl compound.

EXAMPLE 2

The process as described in Example 1 can also be performed in such a manner that an inert gas sweep to remove excess methyl bromide into the dissolving vessel is not required. This advantage is achieved by stopping the methyl bromide addition as soon as the methyl bromide up-take rate substantially diminishes. The residual amount of methyl bromide remaining in the reactor is consumed until the pressure in the reactor diminishes to between about 300 to 400 mm. mercury. After attaining this pressure, the batch of product formed is then worked up in the normal manner.

The following example involves addition of an emulsifier to increase the reaction rate of the alkylation:

EXAMPLE 3

404 g of butylthion are dissolved in 1500 ml of water by addition of 161 g of 50% caustic solution. The aqueous sodium salt solution is charge to a four neck reaction flask equipped with an agitator, a gas inlet tube, a pH probe, a thermometer, a reflux condenser, a dropping funnel for NaOH and a connection to a suction line. After the pH of the solution has been adjusted to 12, 2.5g of the emulsifier NP 10 are added; then the reaction flask is evacuated and with strong agitation 210 g of methyl bromide are added as fast as possible at temperature between 30°–35° C; after 32 minutes the required amount is absorbed. During the addition of the methyl bromide the pH changes from 12.2 to 10.5. For post-reaction the pH is adjusted to 11.5 and the mixture is agitated for 10 minutes at a reaction temperature of 30°–35° C; thereafter the slurry is cooled to 15°–20° C and the precipitated methylated product is isolated by filtration. The yield of crude product is 416 g = 97.2% of theory. Generally under the same reaction conditions without any emulsifier 2 hours are necessary for the addition of the calculated methyl bromide; with 2.0 g of NP 10 the same experiment is completed in 40 minutes. Other emulsifiers show the same rate improvement.

EXAMPLE 4

Into a four-neck flask equipped with an agitator, a gas inlet tube, thermometer, pH probe, and a reflux condenser there is introduced a solution prepared by dissolving 200 g of technical butylthion in 750 ml of a 1:1 mixture of mother liquor and water (containing 53 ml of 50% NaOH). The flask is evacuated and maintained at 30°–32° C and then, under heavy agitation and keeping the pH between 11.0 –11.5 by the addition of caustic, methyl bromide is added as fast as possible. As soon as the absorption of methyl bromide ceases, a situation which can be observed by an increase in pressure inside the reaction flask and easily noticeable on the pressure gauge attached to the reaction system, the feed of methyl bromide is stopped. This involves 119 g of methyl bromide although 95g are required by stoichiometry. The system is then kept for 1 hour at a temperature of 32° C for post-reaction. The pressure gauge indicates a drop from 770 mm Hg to 690 mm Hg, apparently due to a further small consumption of methyl bromide. The reaction flask is then purged with nitrogen to remove all unreacted methyl bromide and the precipitated 4-amino-6-t.-butyl-3-methylmercapto-1,2,4-triazine-5-one is isolated by filtration. Amount of crude product = 204.3 g = 95.5%. The same process run with 200 g of the same technical butylthion but without the mother liquor recycle gave 199.4 g = 93.2% of crude product.

It will be appreciated that the instant specification and examples are set forth by way of illustration and not limitation, and that various modifications and changes may be made without departing from the spirit and scope of the present invention.

What is claimed is:

1. In the process wherein 4-amino-6t.-butyl-3-mercapto-1,2,4-triazine-5-one is reacted with methyl bromide in an alkaline medium to produce a slurry of 4-amino-6t.-butyl-3-methylmercapto-1,2,4-triazine-5-one, the improvement which comprises effecting the reaction in the substantial absence of air.

2. The process of claim 1, wherein an emulsifier is included in the alkaline medium, the reaction rate thereby being at least doubled.

3. The process of claim 1, wherein the methyl bromide is intermittently supplied to a vessel containing the starting material in the alkaline medium, the supply of methyl bromide being shut off when the pressure in the vessel reaches about 1.1 bars.

4. The process of claim 3, wherein the reaction is effected with stirring and with recirculation through a pump, the methyl bromide being supplied to the vessel by discharging it adjacent the outlet from said pump.

5. The process of claim 1, wherein the reaction is effected employing a reactor and dissolving vessel, at the end of the reaction in the reactor the gases therein, including substantially all the unreacted methyl bromide, are bubbled through alkaline medium in the dissolving vessel, the solid product in the slurry in the first vessel is separated, and at least a portion of the liquid from the slurry is recycled to the dissolving vessel for use in a later reaction cycle.

6. The process of claim 5, wherein bubbling of the gases from the reactor is effected by passing nitrogen through said vessel under pressure so as to carry along therewith any residual gases in said vessel.

7. The process of claim 6, wherein an emulsifier is included in the alkaline medium, the reaction being effected in a vessel with stirring and with recirculation through a pump, the methyl bromide being intermittently supplied, the supply of methyl bromide being shut off when the pressure in the vessel reaches about 1.1 bars.

* * * * *